United States Patent [19]

Korber

[11] Patent Number: 5,002,554
[45] Date of Patent: Mar. 26, 1991

[54] MICROSCISSORS DEVICE AND ANASTOMOTIC REPAIR TECHNIQUE

[76] Inventor: Kenneth E. Korber, 4019 Westminster Pl., St. Louis, Mo. 63108

[21] Appl. No.: 444,002

[22] Filed: Nov. 30, 1989

Related U.S. Application Data

[63] Continuation of Ser. No. 183,598, Apr. 19, 1988, abandoned.

[51] Int. Cl.$^5$ .................. A61B 17/00; A41H 25/00; B25B 7/02
[52] U.S. Cl. .................. 606/174; 606/207; 30/120; 30/261; 81/418
[58] Field of Search .......... 606/174, 206, 208, 210, 606/207; 30/118, 120, 261, 245, 258, 178, 316, 363, 186, 192; D24/26, 28; 81/420, 418, 415, 427

[56] References Cited

U.S. PATENT DOCUMENTS

| | | | |
|---|---|---|---|
| 630,455 | 8/1899 | Hazard | 30/120 |
| 681,327 | 8/1901 | Klever, Jr. | 30/120 |
| 3,651,811 | 3/1972 | Hildebrandt | 606/174 |
| 4,299,030 | 11/1981 | Vickers | 30/261 |
| 4,478,221 | 10/1984 | Heiss | 606/174 |
| 4,817,287 | 4/1989 | Arnold et al. | 30/178 |
| 4,823,792 | 4/1989 | Dulebohn et al. | 606/151 |

FOREIGN PATENT DOCUMENTS 1367953 1/1988 U.S.S.R. .................. 128/321

Primary Examiner—Randall L. Green
Assistant Examiner—Gary Jackson
Attorney, Agent, or Firm—Polster, Polster and Lucchesi

[57] ABSTRACT

A microscissors device for us in microvascular end-to-side anastomosis, and an end-to-side vascular anastomotic repair technique are disclosed. The microscissors device standardizes the excision in a recipient (arterial or venous) vessel wall so that a hemodynamically sound anastomosis can be achieved. In order to form the standardized excision, a microscissors device has pivoting arms providing a scissors-action with cooperating half-moon shaped sharpened indentations in the pivoting arms which engage and form the uniform excision in the recipient vessel wall. The end-to-side vascular anastomotic repair technique includes the step of forming a standardized generally longitudinally extending excision in the recipient vessel wall to facilitate insertion and subsequent suturing of the donor vessel, in a hemodynamically sound manner. The excision is made as uninterrupted single-step excision. Also, the excision is formed essentially within the confines of the recipient vessel wall without extending substantially across the passageway of the recipient vessel.

5 Claims, 2 Drawing Sheets

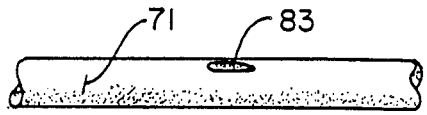
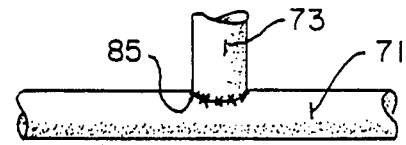
FIG.6.        FIG.7.
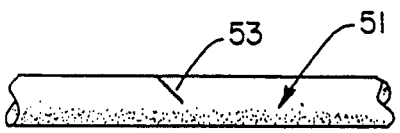
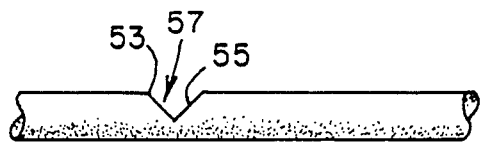
FIG.8.        FIG.9.
PRIOR ART.    PRIOR ART.
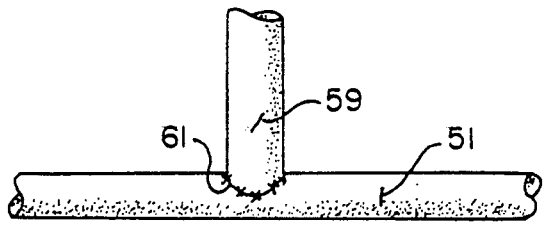
FIG.10.
PRIOR ART.

MICROSCISSORS DEVICE AND ANASTOMOTIC REPAIR TECHNIQUE

BACKGROUND OF THE INVENTION

The present invention relates to a microscissors device for use in microvascular end-to-side anastomosis, and to an end-to-side vascular anastomotic repair technique.

Normal blood flow in a vessel (arteries and veins) is smooth and laminar, with blood flow determined by the pressure differential across the vessel and the resistance to flow offered by the vessel. As the diameter of a vessel decreases, there is a rise in the resistance to the flow of blood. Other factors affecting blood flow include the oscillatory stress or pulsating pressure in arteries, and vessel branching or bifurcation. The latter factor, vessel branching or bifurcation, is very important in microvascular surgery of reconstructed vessels.

Microvascular reconstruction is a reliable procedure when both donor and recipient vessels are normal; however, the success of reconstruction procedures in arterial and venous microsurgery largely depends on the union or anastomotic patency of the reconstructed vessels. If there is any obstruction in the reconstructed vessels, vascular thrombosis or clotting may result.

Generally, two procedures are employed in microvascular surgery of reconstructed vessels. One conventional technique is an end-to-end (ETE) anastomosis where the ends of the vessels are sutured together. The other technique is end-to-side (ETS) anastomosis. The present invention relates to the latter technique.

Historically, surgeons performing an end-to-side (ETS) anastomosis have made two angular and intersecting incisions forming a generally v-shaped excision in the recipient vessel at the planned donor implantation site. In order to make these incisions as close as possible to the approximate size and dimension of the donor vessel, the surgeon is required to make multiple manipulations of the vessel along with a final trimming maneuver.

There have been several attempts by experienced microsurgeons to bypass this method of recipient vessel preparation. These have included placing a suture through the vessel wall and using the tails of these sutures as a traction device, causing a "tenting" of the arterial or vein wall. This "tented" region is then excised with microscissors. While the "tented" region affords the surgeon a better opportunity and greater vision to make the desired excision, surgeons still have little control over the size and shape of the excision.

As has been explained above, any obstruction to normal blood flow in vessels is undesirable. Unfortunately, the aforementioned end-to-side anastomotic repair techniques may result in a vessel obstruction, due to non-uniformities in forming the excision at the desired location. Suturing of the donor and recipient vessel in the excised area also does not alleviate the damage already done by a non-uniform and unreliable excision made in the recipient vessel wall.

SUMMARY OF THE INVENTION

Among the several objects and features of this invention may be noted:

The provision of a microscissors device for use in microvascular end-to-side anastomosis;

The provision of the aforementioned microscissors device which provides consistent and reproducible results in making desired excisions for end-to-side anastomotic repairs, in order to provide a surgically efficient, and hemodynamically sound anastomosis;

The provision of the aforementioned microscissors device which enables a single pass or cut of the microscissors device to form the desired excision in a recipient vessel wall for receipt of the donor vessel; and The provision of the aforementioned microscissors device which conforms the size and shape of the excision made in the recipient vessel to the corresponding size and shape of the donor vessel, by preselecting the correctly sized and shaped microscissors device.

A microscissors device of the present invention is designed for use in performing end-to-side (ETS) vascular anastomotic repairs. The device includes a pair of elongated arms pivotally mounted adjacent one end thereof, the opposite end of the arms being capable of moving the arms about the pivot mount with each of the arms between the pivot mount and the adjacent end having a generally longitudinally extending straight-edge surface in close proximity to one another to produce a scissors-action between the surfaces as they move past one another. Each of the arms has mirror-image, generally half-moon shaped fully overlappable indentations formed therein, the indentations being generally intermediate the length of the longitudinally extending surface of the arms and centered generally midway therealong. The indented portion of each arm is sharpened to form a cutting edge so that when the device is used on a hollow vessel to be repaired, a generally uniform, slightly oval shaped excision in the wall of the vessel is made with a single cutting step.

Other objects and features of this invention will become apparent from the description that follows.

BRIEF DESCRIPTION OF THE DRAWINGS

FIG. 6 is a further fragmentary perspective view illustrating the uniform excision formed in the wall of the recipient vessel;

FIG. 7 is another fragmentary perspective view showing the free end of the donor vessel sutured around the margins of the excision in the recipient vessel;

FIG. 8 is a fragmentary perspective view of one common prior art technique beginning with an angular incision into the recipient vessel;

FIG. 9 is a still further fragmentary perspective view illustrating the next step in the prior art technique including a second angular incision formed in the recipient vessel to provide an excision in the recipient vessel for receiving the donor vessel; and FIG. 10 is a further fragmentary diagrammatic perspective view illustrating the manner of suturing the free end of a donor vessel to a recipient vessel having an excision formed therein as shown in the prior art technique of FIGS. 8 and 9.

Corresponding reference characters indicate corresponding parts through the several views of the drawings.

DESCRIPTION OF THE PREFERRED EMBODIMENT

Figure 1:
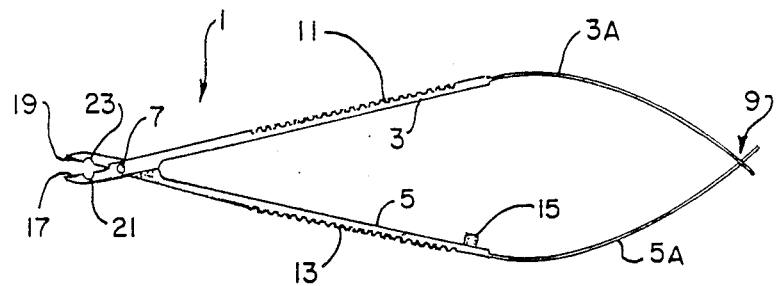
FIG. 1 is a side elevational view showing one form of microscissors device which is constructed in accordance with the teachings of the present invention.
Figure 2:
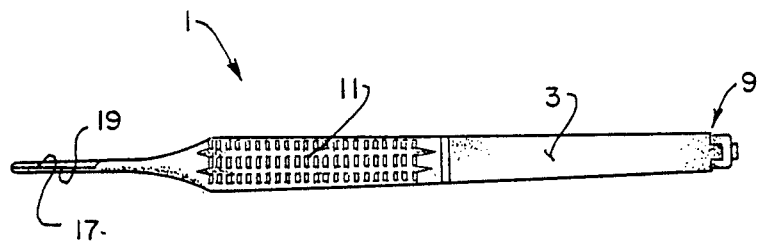
FIG. 2 is a top plan view of the microscissors device shown in FIG. 1.
Figure 3:
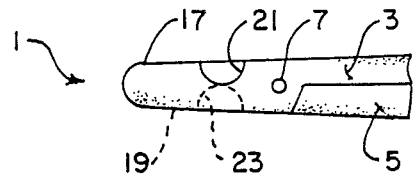
FIG. 3 is an enlarged fragmentary side elevational view showing the manner in which the blades of a microscissors device of FIG. 1 cooperate to form uniform excisions in hollow vessel walls.

FIGS. 1 through 3 show a microscissors device 1 in which pivotally mounted arms are normally spring biased apart from one another. More particularly, microscissors device 1 includes a pair of upper and lower elongated arms 3, 5 respectively which are pivotally mounted at 7 adjacent one end of the arms 3, 5. At the opposite end of arms 3, 5 are disposed spring arms 3A, 5A fitted together at their proximal end by an interfitting connection, such as the complementary tongue and groove connection 9, to assist in maintaining arms 3 and 5 in a spring biased portion as illustrated in FIG. 1.

Upper and lower arms 3, 5 are each provided with other knurled surfaces 11, 13 which facilitate gripping of microscissors device 1. Lower arm 5 includes an upwardly extending stop or abutment 15. Stop 15 is designed to engage the under surface of the upper arm 3 in limiting closing movement of arms 3, 5 when the cooperating blade portions, to be described below, have completed their cooperating interfitting movement relative to one another, and also to assist in preventing separation of arms 3, 5 at the complementary tongue and groove connection 9.

Upper and lower arms 3, 5 between pivotal mount 7 and the adjacent end of each arm present generally longitudinally extending straight edge surfaces 17 (on upper arm 3) and 19 (on lower arm 5) which are in close proximity to one another, as shown in the top plan view of FIG. 2. This provides a scissors-action between the cooperating straight-edge surfaces 17, 19 when these surfaces are moved passed one another.

Figure 4:
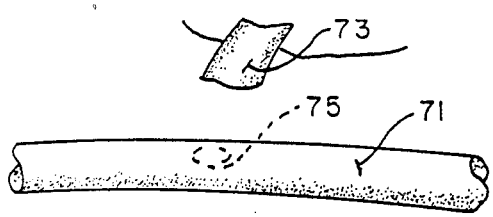
FIG. 4 is fragmentary perspective view illustrating donor and recipient vessels which are to be joined together in microvascular end-to-side anastomotic repair.
Figure 5:
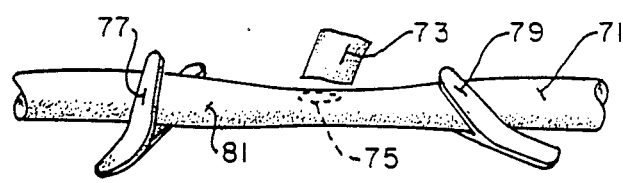
FIG. 5 is a also a fragmentary perspective view which illustrates clamping the recipient vessel on opposite sides of an area to be excised for receipt of the donor vessel.

Longitudinally extending surfaces 17 and 19 are provided with mirror-image, generally half-moon shaped sharpened indentations. Indentation 21 is formed in straight-edge surface 17 of upper arm 3, and indentation 23 is formed in straight-edge surface 19 of lower arm 5. These sharpened half-moon indentations cooperate with one another to form the uniform excision in the circumferentially extending wall of a hollow vessel, such as shown in FIGS. 4-6 of the drawings.

Referring to FIG. 3 of the drawings, it will be seen that when upper and lower arms 3, 5 are closed by manually compressing the upper and lower spring arms 3A and 5A, the sharpened half-moon shaped indentation 21 formed in the straight-edge surface 17 of upper arm 3 overlaps and crosses over the sharpened half-moon indentation 23 formed in the straight edge surface 19 of the lower arm 5. Since the straight edged surfaces are in close proximity to one another in order to provide a scissor action between such surfaces, the half-moon indentations 21, 23 provide a uniform excision in a circumferentially extending wall of a hollow vessel, such as shown in FIG. 6 of the drawings. In FIGS. 4 and 5, the slightly oval-shaped dotted-line illustrates the desired excision in the hollow recipient vessel, and FIG. 6 shows the uniform excision that can be made in the circumferentially extending wall of the hollow vessel. It is to be noted that since the vessel is cut when clamped as shown in FIG. 5 of the drawings, a slightly oval configuration for the uniform excision may be produced.

The generally longitudinally extending straight-edge surfaces 17, 19 in the microscissors device of FIGS. 1-3 are angularly offset from a longitudinal center line extending through the pivotal mount in microscissors devices 1, as shown in FIG. 1 of the drawings. Also, it will be noted that the half-moon shaped indentations 21, 23 in microscissors device 1 are provided generally intermediate the length of the generally longitudinally extending surfaces in microscissors device 1. Since the half-moon shaped indentations 21, 23 in the microscissors device 1 are the only sharpened areas in their respective surfaces, cutting action only at those particular indentations is assured.

Microscissors devices having different sized half-moon shaped indentations may be selected to form a variety of different-sized excisions in a hollow vessel, as may be desired. Where surgically indicated, such as in gynecological and genitourinary microsurgical procedures, the half-moon shaped indentations may be serrated. Moreover, while the microscissors device of this invention is primarily used for microsurgery, it is also usable in vascular surgery in general with a simple change in scale.

The end-to-side microvascular/vascular anastomotic repair technique of the present invention will be best understood by reference to FIGS. 4-10 of the drawings. In FIGS. 8-10 of the drawings (representing prior art techniques), the hollow recipient vessel 51 has a pair of angular or inclined and intersecting incisions 53, 55 cut therein by a standard microscissors device in order to form the v-shaped excision 57.

Because of multiple manipulations and additional trimming of the v-shaped excision 57 which is necessary in the prior art technique to conform to the shape of a hollow vessel 59 (as seen in FIG. 10 of the drawings), substantial potential exists for disruption of normal blood flow through the reconstructed vessels 51, 59 following anastomosis by sutures 61. This is due primarily to non-uniformities in v-shaped excision 57 cut in the hollow recipient vessel 51. Because of these non-uniformities, some tissue folds or flaps can extend within the passageways of vessels 51 and 59.

The end-to-side vascular anastomotic repair technique using the microscissors device of the present invention (shown in FIGS. 4-7) substantially avoids the problems encountered in the above-described prior art techniques, as well as those prior art techniques utilizing "tenting" of the recipient vessel as described in the background of the invention.

In order to join a recipient vessel 71 to a vessel 73 in an end-to-side vascular anastomotic surgical reconstruction, an excision 75, shown in phantom lines, must be formed in the circumferentially continuous wall of hollow recipient vessel 71 as shown in FIG. 4 of the drawings. The desired excision 75 is shown as being slightly oval-shaped and extending generally longitudinally along the elongated recipient vessel 71. This slightly oval or elliptical shape of the desired excision 75 as shown in FIG. 5 may be caused by the clamping of the recipient vessel on opposite sides of the area 81 to be excised, by means of a pair of clamps 77 and 79.

Following the clamping of the recipient vessel 71, a standardized longitudinally extending excision 83 is formed in the recipient vessel 71, as shown FIG. 6 of the drawings. Excision 83 corresponds to the desired excision 75 of FIGS. 4 and 5. The standardized longitudinally extending excision 83 in the recipient vessel 71 is generally complementary shaped and dimensioned relative to the exterior circumferential dimension of the circumferentially continuous wall of vessel 73. As has been discussed in connection with FIGS. 1–3, this standardized excision is formed by the microscissors device 1 in order to eliminate the deficiencies associated with prior art techniques.

The standardized excision 83 is formed in the recipient vessel 71 as an uninterrupted single-step excision, whereas the prior art required interrupted multiple step excisions. Furthermore, the standardized excision 83 is formed essentially within the confines of the circumferentially continuous wall of the recipient vessel 71 without extending substantially transversely to or across the recipient vessel 71, as occurs in connection with the prior art techniques. Thus, when it is desired to suture the free end of vessel 73 to the recipient vessel 71 in the area surrounding the standardized excision 83, suturing 85 may be achieved without having an unnecessary tissue folds or flaps extending within the hollow passageways of vessels 71 and 73.

From the foregoing, it will be appreciated that proper alignment, positioning and suturing of vessels 71 and 73 may be achieved through the standardized and uniform excision 83 formed in the recipient vessel 71. The uninterrupted single-step excision 83 formed essentially within the confines of the recipient vessel 71, without extending substantially transverse to or across the passageway of recipient vessel, as in prior art techniques, minimizes the possibilities of any obstructions being present within the reconstructed vessel which would inhibit normal blood flow. In addition, the simplicity, efficiency and ease of the end-to-side anastomotic repair technique using the microscissors device of the present invention overcomes the difficulties associated with prior art techniques, as will now be understood.

In view of the above, it will be seen that the several objects of the invention are achieved and other advantageous results are obtained.

As various changes could be made in the above constructions and method without departing from the scope of the invention, it is intended that all matter contained in the above description or shown in the accompanying drawings shall be interpreted as illustrative and not in a limiting sense.

What is claimed is:

1. A microscissors device for use in performing end-to-side (ETS) vascular anastomotic repairs comprising a pair of elongated arms pivotally mounted adjacent one end thereof, the opposite end of the arms being capable of moving the arms about the pivot mount with each of the arms between the pivot mount and the adjacent end having a generally longitudinally extending straight-edge surface in close proximity to one another to produce a scissors-action between the surfaces as they move past one another, each of the arms having mirror-image, generally half-moon shaped fully overlappable indentations formed therein, the indentations being generally intermediate the length of the longitudinally extending surface of the arms and centered generally midway therealong, the indented portion of each arm being sharpened to form a cutting edge whereby when the device is used on a hollow vessel to be repaired, a generally uniform, slightly oval shaped excision in the wall of the vessel is made with a single cutting step.

2. The microscissors of claim 1 wherein the generally longitudinally straight-edge surfaces are angularly offset from a longitudinal centerline extending through the pivotal mount.

3. The microscissors of claim 2 wherein the arms are spring arms for the opposite ends of the arms to be normally spring-biased apart from each other.

4. The microscissors of claim 3 further including means for interlocking the opposite ends of the arms.

5. The microscissors of claim 4 wherein the opposite ends of the arms form a complementary tongue and groove connection.

* * * * *